US008664250B1

(12) United States Patent
Ross et al.

(10) Patent No.: US 8,664,250 B1
(45) Date of Patent: *Mar. 4, 2014

(54) SYNERGISTIC COMBINATION OF FUNGICIDES TO PROTECT WOOD AND WOOD-BASED PRODUCTS AND WOOD TREATED BY SUCH COMBINATION AS WELL AS METHODS OF MAKING THE SAME

(75) Inventors: Alan S. Ross, Pittsburgh, PA (US); Brian Marks, Pittsburgh, PA (US); Hans Ward, Wexford, PA (US)

(73) Assignee: Kop-Coat, Inc., Pittsburgh, PA (US)

( * ) Notice: Subject to any disclaimer, the term of this patent is extended or adjusted under 35 U.S.C. 154(b) by 1596 days.

This patent is subject to a terminal disclaimer.

(21) Appl. No.: 11/130,526

(22) Filed: May 17, 2005

Related U.S. Application Data

(62) Division of application No. 10/351,021, filed on Jan. 24, 2003, now Pat. No. 7,056,919.

(51) Int. Cl.
*A01N 43/653* (2006.01)
*A01N 47/12* (2006.01)
*A01N 41/10* (2006.01)
*A01N 33/24* (2006.01)
*B27K 3/34* (2006.01)
*B27K 3/38* (2006.01)
*B27K 3/50* (2006.01)

(52) U.S. Cl.
CPC . *B27K 3/34* (2013.01); *B27K 3/343* (2013.01); *B27K 3/38* (2013.01); *B27K 3/50* (2013.01); *A01N 43/653* (2013.01); *A01N 47/12* (2013.01); *A01N 41/10* (2013.01); *A01N 33/24* (2013.01); *A01N 2300/00* (2013.01)
USPC .......... 514/383; 514/479; 514/644; 514/645; 514/646; 514/709; 424/405

(58) Field of Classification Search
CPC ..... A01N 43/653; A01N 47/12; A01N 41/10; A01N 33/24; A01N 2300/00; B27K 3/34; B27K 3/343; B27K 3/38; B27K 3/50
USPC .......... 424/405; 514/383, 479, 644, 645, 646, 514/709
See application file for complete search history.

(56) References Cited

U.S. PATENT DOCUMENTS

| 4,552,885 | A | 11/1985 | Gabriele et al. |
|---|---|---|---|
| 4,879,083 | A | 11/1989 | Knudson et al. |
| 4,950,685 | A | 8/1990 | Ward |
| 5,223,524 | A | 6/1993 | Valcke |
| 5,389,300 | A | 2/1995 | Schmitt et al. |
| 5,763,338 | A | 6/1998 | Sean |
| 5,804,591 | A | 9/1998 | Valcke et al. |
| 5,846,305 | A | 12/1998 | Payzant |
| 5,880,142 | A | 3/1999 | Otsu et al. |
| 5,948,730 | A | 9/1999 | Kuusisto et al. |
| 5,972,266 | A | 10/1999 | Fookes et al. |
| 5,985,301 | A | 11/1999 | Nakamura et al. |
| 5,990,043 | A | 11/1999 | Kugler et al. |
| RE36,798 | E | 8/2000 | Williams et al. |
| 6,153,648 | A | 11/2000 | Makino et al. |
| 6,340,384 | B1 | 1/2002 | Walker |
| 6,375,727 | B1 | 4/2002 | Walker |
| 6,527,981 | B1 | 3/2003 | Tseng et al. |
| 2003/0096545 | A1 * | 5/2003 | Payne ............... 442/123 |

FOREIGN PATENT DOCUMENTS

| WO | WO 00/71314 | 11/2000 |
|---|---|---|
| WO | WO 01/89779 | 11/2001 |

OTHER PUBLICATIONS

J. J. Morrell et al., "Preventing Discoloration of Unseasoned Hem-Fir and Douglas-Fir Lumber with Selected Fungicide Formulations", Forest Products Journal, Feb. 2002. pp. 53-61. vol. 52, No. 2, Forest Products Society, Madison, Wisconsin.

* cited by examiner

*Primary Examiner* — Kortney L Klinkel
(74) *Attorney, Agent, or Firm* — Eckert Seamans Cherin & Mellott, LLC; Arnold B. Silverman

(57) ABSTRACT

A wood treatment composition having a synergistic combination of fungicides which may include two or more compounds. These combinations are shown to be especially effective in providing resistance to decay, mold and mildew when wood is treated with these combinations. Also provided is wood treated by these combinations, and a method of treatment for composite wood.

18 Claims, No Drawings

SYNERGISTIC COMBINATION OF FUNGICIDES TO PROTECT WOOD AND WOOD-BASED PRODUCTS AND WOOD TREATED BY SUCH COMBINATION AS WELL AS METHODS OF MAKING THE SAME

CROSS-REFERENCE TO RELATED APPLICATIONS

The present application is a divisional of U.S. Ser. No. 10/351,021 filed Jan. 24, 2003 now U.S. Pat. No. 7,056,919.

BACKGROUND OF THE INVENTION

1. Field of the Invention

This invention relates to synergistic combinations of fungicides which, when applied to wood, give a synergistic result in providing improved resistance to mold, mildew and fungal decay. Wood treated with this combination, and a method of treating wood, are also included in the present invention.

2. Description of the Prior Art

Wood is one of the best structural materials for the construction of buildings because of its strength, ease of processing and relatively low cost. However, wood and wood-based materials, including cellulosic composites and plastic-wood composites, are susceptible to attack from various fungal organisms. Fungal attack can result in cosmetic damage (stain, mold and mildew) and/or structural degradation (decay) to both solid wood and wood-based composites.

Mold organisms, in addition to marring the appearance of wood, can present a health hazard in indoor environments since certain mold spores have the potential to be human respiratory allergens.

Sapstain is a particular problem for freshly sawn green lumber. Although attack by sapstain fungi does not generally result in the reduction of strength properties, sapstain can seriously degrade the value of lumber by impairing its appearance.

Preservative chemicals have been used since antiquity to prevent the onset of mold, stain and decay to wood in service. In recent times, the use of some wood preserving chemicals has been restricted or curtailed due to concerns about their safety to humans and their effects on the environment. Cost effectiveness of preservative treatments is also a major consideration since wood ultimately competes with non-cellulosic construction materials including steel, plastic and concrete.

Currently, a variety of fungicides are available to protect wood and wood composites from fungal attack. For example, it is known to use zinc borate to protect cellulosic composites, including particleboard, hardboard and oriented strand board, from fungal decay, as described in U.S. Pat. Nos. 4,879,083; 5,763,338; and 5,972,266. However, like most borates, zinc borate is not particularly effective against mold fungi. Recent work by Kop-Coat, Inc. (U.S. Pat. No. 6,416,789) has shown that combinations of IPBC, amine oxides and borates have a synergistic effect against many types of fungus in panel products such as OSB and hardboard.

Beginning in the 1930s, the sodium salt of pentachlorophenol (PCP) was the chemical of choice in preventing sapstain discoloration in freshly sawn lumber. By the mid-1980s, PCP was restricted for this use due to concerns over safety and environmental impact. This led to the development of a number of substitutes based on preservatives such as TCMTB, IPBC and DDAC. One of the leading antisapstain formulas continues to be NP-1®, a synergistic mixture of IPBC and DDAC (U.S. Pat. No. 4,950,685). New formulas have been developed in recent years. The performance of many of these has been evaluated by Oregon State University. (See Forest Products Journal Vol. 52, No. 2, pp 53-61 for a review of recent formulas.)

Since the 1940s, the main products for pressure treating have been creosote, PCP in fuel oil and CCA. In February 2002, the U.S. EPA restricted the use of CCA in residential applications of pressure treated wood, effective Dec. 31, 2003. Alternative treatments include borates, copper azole and ACQ.

Millwork treatment is a non-pressure application of preservatives to protect against mildew and decay. Solid lumber or wood composites are generally dipped in millwork treating solutions which also contain water repellents. WDMA Standard I.S. 4-2000 covers the preservative treatment of millwork components. Products approved under WDMA Hallmark Certification Program are based on TBTO, IPBC, TCMTB, propiconazole and tebuconazole. Synergistic antifungal combinations of propiconazole and tebuconazole are the subject of U.S. Pat. No. 5,223,524.

In recent years, there have been increasing concerns about mold growth in indoor residential environments. Mold can be a respiratory allergen to some individuals and is suspected of being a toxin in extreme exposure situations, although evidence of toxicity to humans is in question. Manufacturers of panel products such as OSB are taking steps to reduce or eliminate the possibility of mold growth on their materials. Potlatch Corporation has introduced OX-Terminator, a wood preservative treated panel product. See, e.g., International Application Publication No. WO 01/79339 A1. The active ingredient is based on a copper ammonium complex.

It is also known to use iodopropargyl derivatives such as 3-iodo-2-propynyl-n-butyl carbamate (IPBC) for protection against fungi which cause structural and cosmetic damage to wood. However, while effective, this compound used alone is expensive and requires larger amounts to achieve the desired end result.

U.S. Pat. No. 5,389,300 provides a composition for protecting sawn timber against wood discoloring fungi, containing a phenol fungicide and a halopropynyl fungicide such as IPBC. Other fungicides, insecticides, or active ingredients, including boron compounds, can be added to the composition.

U.S. Pat. No. 5,846,305 discloses a wood preservative composition comprising a copper compound, an amine solvent and a boron compound. The preferred boron compound is sold by U.S. Borax, Inc. under the tradename "TIM-BOR."

U.S. Pat. No. Re36,798 provides a preservative composition for treatment of wood and other cellulosic materials, comprising a biocidal metal compound and a fungicidal compound containing a triazole group. Compositions of this invention may contain other organic fungicides, insecticides, or bactericides, including boron in any form, such as boric acid, boron, or boron esters.

U.S. Pat. No. 4,950,685 relates to a wood preservative composition which provides stain resistance to wood. The composition comprises a synergistic combination of a quaternary ammonium compound and IPBC.

U.S. Pat. No. 5,990,043 relates to an anti-fouling composition which includes a carrier, a binder, and an effective amount of at least one insecticide, which can be a carbamate. Synergistic effects are observed when combinations of two or more of the numerous insecticides listed are used in combination.

It is desired, therefore, to develop a wood treatment substance capable of protecting wood against fungal decay, mold and mildew in an economical, safe and environmentally responsible manner.

SUMMARY OF THE INVENTION

The present invention fulfills the above need by providing an unusually effective and economical wood treatment that protects wood and wood products against fungal decay, mold and mildew. The present invention provides unique combinations of four classes of fungicides, specifically azole compounds, halopropynyl compounds, amine oxide compounds and diiodomethyl-p-tolylsulfone, which in combination provide a more complete resistance to decay, in a more economical manner, than use of any of these compounds individually. A method of treating wood, in particular composite wood materials, with the synergistic combination is included in the present invention, as is the wood treated by this combination.

Depending on the desired level of protection, combinations of two or three compounds can also be used.

The present invention offers a meaningful advantage over many currently utilized wood preservative products. It has a favorable health/safety/environmental profile, and it offers a very cost-effective method of protecting wood and wood-based composites from various forms of fungal attack.

It is an object of the invention therefore, to provide a combination of fungicides to resist decay, mold and mildew in wood treated with such substances, in an economical manner.

It is a further object of the present invention to provide an economical wood treatment which can resist decay using azoles in combination with halopropynyl, amine oxide and diiodomethyl-p-tolylsulfone.

It is an additional object of the present invention to provide a method of treating wood using this synergistic combination of fungicides.

It is an additional object of the present invention to provide wood treated with a synergistic combination of fungicides.

It is an additional object of the present invention to provide a wood treatment composition that is biodegradable in soil and has an excellent worker safety and environmental profile.

These and other objects of the invention will become apparent from the following description and appended claims.

DETAILED DESCRIPTION OF PREFERRED EMBODIMENTS

Accordingly, the present invention provides a wood treatment composition comprising a synergistic combination of an azole compound, a halopropynyl compound, an amine oxide compound and diiodomethyl-p-tolylsulfone. As used herein, the term "wood treatment composition" refers to this synergistic combination of fungicides, which may be used with other additives such as resins or solvents, and which is applied to wood by a variety of methods including, but not limited to, spraying, dipping, pressure treating, addition to wood furnish during formation of wood composites, and other methods used to apply such substances to wood and are known to those skilled in the art.

As used herein, an azole compound refers to a 1,2,4-triazole. Suitable azoles include, but are not limited to, triadimefon, triadimenol, triazbutil, propiconazole, cyproconazole, difenoconazole, fluquinoconazole, tebuconazole, flusiazole, uniconazole, diniconazole, bitertanol, hexaconazole, azaconazole, flutriafol, epoxiconazole, tetraconazole, penconazole, and mixtures thereof.

As used herein, the term "halopropynyl compound" refers to a category of halopropynyl compounds known to have biocidal activity and to provide protection against fungi when applied to wood and other materials.

Suitable examples of halopropynyl compounds which may be used in the present invention include, but are not limited to, iodopropargyl derivatives including compounds derived from propargyl or iodopropargyl alcohols such as the esters, ethers, acetals, carbamates and carbonates and the iodopropargyl derivatives of pyrimidines, thiazolinones, tetrazoles, triazinones, sulfamides, benzothiazoles, ammonium salts, carboxamides, hydroxamates, and ureas. This class of compounds has the general formula:

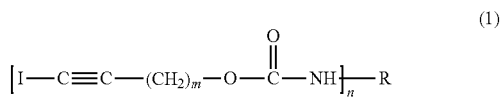

(1)

wherein R is selected from the group consisting of hydrogen, substituted and unsubstituted alkyl groups having from 1 to 20 carbon atoms, substituted and unsubstituted aryl, alkyl aryl, and aralkyl groups having from 6 to 20 carbon atoms and from substituted and unsubstituted cycloalkyl and cycloalkenyl groups of 3 to 10 carbon atoms, and m and n are independently integers from 1 to 3, i.e., m and n are not necessarily the same.

Preferred are formulations where m is 1 and n is 1 having the following formula:

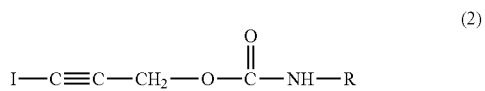

(2)

Suitable R substituents include alkyls such as methyl, ethyl, propyl, n-butyl, t-butyl, pentyl, hexyl, heptyl, octyl, nonyl, decyl, dodecyl, octadecyl, cycloalkyls such as cyclohexyl, aryls, alkaryls and aralkyls such as phenyl, benzyl, tolyl, cumyl, halogenated alkyls and aryls, such as chlorobutryl and chlorophenyl, and alkoxy aryls such as ethoxyphenyl and the like.

Compounds of this formula include iodopropargyl carbamates such as 3-iodo-2-propynyl propyl carbamate, 3-iodo-2-propynyl butyl carbamate, 3-iodo-2-propynyl hexyl carbamate, 3-iodo-2-propynyl cyclohexyl carbamate, 3-iodo-2-propynyl phenyl carbamate, and mixtures thereof. Most preferred is 3-iodo-2-propynyl butyl carbamate (IPBC).

As used herein, the term "amine oxide compound" refers to those compounds which are formed as reaction products in the reaction of tertiary amines and hydrogen peroxides and are represented by the general formula:

(3)

where $R_1$, $R_2$ and $R_3$ are independent and can be a linear, branched, cyclic, aromatic or any combination thereof of saturated or unsaturated $C_1$ to $C_{20}$ group and any $C_2$-$C_{20}$ carbon atom can be replaced with a hetero-atom selected from the group consisting of O, S and N.

Preferred amine oxides are alkyl dimethyl amine oxides such as decyl dimethyl amine oxide, lauryl dimethyl amine oxide, isoalkyl dimethyl amine oxide, myristyl dimethyl amine oxide, cetyl dimethyl amine oxide, stearyl dimethyl amine oxide and octyl dimethyl amine oxide. Most preferred is N-alkyl(C12-C16)-N,N-dimethylamine oxide (ADO).

As used herein, the term "wood" includes a variety of wood and wood-based materials, including, but not limited to, logs, dried lumber, green lumber, fiberboard, strand board, laminated veneer lumber, cellulosic composites, plastic wood composites and other types of wood, wood composites and engineered wood formed from wood flakes, chips, strands, veneers and adhesives. The wood treatment composition may be applied to any wood substrate to prevent sapstain and other types of fungal attack. With green lumber, meaning freshly cut or unseasoned lumber, it is desirable to control sapstain and mold.

Typically, the four compounds are mixed together sequentially with solvents and other additives, the mixing comprising light agitation, to obtain a clear solution after each addition. The diiodomethyl-p-tolylsulfone must be mixed with the amine oxide in the first step and agitated until a clear solution is obtained. The order of addition of the other ingredients is otherwise unimportant.

Any organic solvent can be used, but polar organic solvents are preferred as they will provide better solubilization of the halopropynyl compound. Additional suitable solvents include, but are not limited to, alcohols, glycols, esters, ethers, polyethers and amines. Most preferred are solvents such as dipropylene glycol monomethyl ether.

Other constituents of the solution may include wax emulsion or other water repellant, solvents and/or water. Additional additives may also be used, and suitable additives include, but are not limited to, corrosion inhibitors, iron stain inhibitors, wetting agents, adhesives, emulsifiers, fillers, carriers, viscosity regulators, colorants, pH regulators, binders, tackifiers, and mixtures of any of these.

In a method of creating the wood product, the fungicide mixture can be applied on the surface of the wood, as in spraying or dipping the wood in a formulation containing all four fungicides. The fungicides can also be applied to the wood with pressure treatment that is commonly used on solid or engineered wood. Another method, particularly for wood composites, is to treat the wood chips, flakes or strands with the fungicide combination in powder or liquid form prior to formation of the composite wood boards.

In this method, the fungicides are combined with wood flakes, chips or strands, an adhesive such as a phenolic or isocyanate resin or other similar resin known to those skilled in the art, and a water repellant and fabricated into a wood composite board. This last step may be accomplished in a heated high-pressure press.

Wood may be treated by more than one of these methods, and as used herein the term "treatment" refers to any one of these or other methods known to those skilled in art and which are used to apply these or similar substances to wood. Other suitable methods include, but are not limited to, spraying, soaking, immersing, vacuum impregnation and brushing, in addition to those already described.

Typically, the wood treatment composition of the present invention will be prepared in concentrate form, and will be diluted prior to application to the wood. As used herein, the term "treating solution" will refer to the wood treatment composition after dilution, as applied to wood.

In concentrate form, the wood treatment composition will comprise about 0.1 to 10% by weight of an azole compound, about 0.1 to 10% by weight of a halopropynyl compound, about 0.1 to 10% by weight of diiodomethyl-p-tolylsulfone and about 5 to 90% by weight of an amine oxide, based upon 100% by weight of the total wood treatment composition. Preferred ranges for amounts of each of the azole, halopropynyl compounds and diiodomethyl-p-tolylsulfone are about 0.1 to 8% by weight of the total composition; most preferred is 0.2 to 6% by weight. The preferred range for the amine oxide is about 10 to 60%, more preferably about 25 to 45%, based on 100% by weight of the total wood treatment composition.

The combination of three of the active ingredients, the azole and halopropynyl compounds and the diiodomethyl-p-tolylsulfone, will comprise about 0.1 to about 30% by weight of the total wood treatment composition in concentrate form, more preferably 0.1 to 20%, most preferably 0.1 to 10%. Thus, as will be understood by one skilled in the art, when less than all three of these compounds are used, the amounts of the remaining ingredients must be adjusted upward to provide the desired overall concentration of active ingredients.

A treating solution, as that term is defined above, can be made from the concentrate wood treatment composition, at the desired dilution level. For example, the concentrate can be diluted with water in a ratio of 300:1 (water:concentrate), 200:1, 150:1, or other dilution ratio. The appropriate dilution level can be determined by one skilled in the art, based on financial considerations, the type of wood being treated, the environmental conditions, and the length of time protection is desired. The amount of each ingredient in the treating solution will thus be the concentrate amount divided by the dilution ratio, for example, if the halopropynyl compound is present in the concentrate in an amount of 8%, based on the total weight of the concentrate, then the amount in the treating solution after a 150:1 dilution will be 0.053% by weight.

In an additional embodiment, less than all four of the fungicides may be used in various combinations of two or three fungicides. For example, suitable combinations include the iodo-sulfone with a halopropynyl compound, iodo-sulfone with an azole, or iodo-sulfone with an amine oxide. IPBC can be used in combination with an azole, or in combination with an amine oxide. This list is not meant to be exhaustive, and use of other combinations of two or three of the above fungicides as a wood treatment composition is contemplated in the present invention. It will be understood by one skilled in the art that depending on the environment in which the treated wood will be used, the type of wood (e.g., green lumber vs. dried lumber), the time duration of protection desired, cost of ingredient, and other similar factors, that use of less than all four ingredients may be desirable and may provide sufficient protection against fungal attack.

The invention is further defined in the following non-limiting examples.

Example 1

One (1) g of Amical 48 (97-99% diiodomethyl-p-tolylsulfone, available from Dow Chemical) and 62.00°g of Barlox 1260PG (60% N-alkyl(C12-C16)-N,N-dimethylamine oxide, 25% propylene glycol, 15% water, available from Lonza), were added together and mixed until solution was clear. 8.25 g of Glycol DPM (100% dipropylene glycol monomethyl ether, available from Shell, Arco Chemical) was added to mixer and allowed to mix until solution was clear.

0.1 g of a defoamer was added to the mixture and mixed until completely dispersed. 1.0 g of a deodorizer was added to mixture, and the entire solution was mixed until clear. 8.75 g of Polyphase AF-1 (40% 3-iodo-2-propynyl-n-butyl carbamate, available from Troy Chemical Co.) was added to mix and agitated until solution is clear. 7.0 g of Wocosen 50 TK (50% propiconazole, 50% dipropylene glycol monomethyl ether, available from Janssen) was added to tank mixture and then agitated until solution was clear. Finally, 11.90 g of a surfactant was added to the tank and mixed for 30 minutes until a clear solution was obtained.

TABLE 1

|  | 50 to 1 | 100 to 1 | 150 to 1 | 200 to 1 | 300 to 1 |
| --- | --- | --- | --- | --- | --- |
| Formula |  |  |  |  |  |
| Amical | 0.02000 | 0.01000 | 0.00667 | 0.00500 | 0.00333 |
| Wocosen 50 TK | 0.14000 | 0.07000 | 0.04667 | 0.03500 | 0.02333 |
| Polyphase AF-1 | 0.17500 | 0.08750 | 0.05833 | 0.04375 | 0.02917 |
| Barlox 12-60 PG | 1.24000 | 0.62000 | 0.41333 | 0.31000 | 0.20667 |
| Inerts |  |  |  |  |  |
| Glycol DPM | 0.16500 | 0.08250 | 0.05500 | 0.04125 | 0.02750 |
| Surfactant | 0.23800 | 0.11900 | 0.07933 | 0.05950 | 0.03967 |
| Deodorizer | 0.02000 | 0.01000 | 0.00667 | 0.00500 | 0.00333 |
| Defoamer | 0.00200 | 0.00100 | 0.00067 | 0.00050 | 0.00033 |

TABLE 2

FORMULATION NUMBER: KC30-21
PRODUCT NAME:

| RAW MATERIAL | WEIGHT | PERCENT BY WEIGHT |
| --- | --- | --- |
| Amical | 1.000 | 1.000 |
| Wocosen 50 TK | 7.000 | 7.000 |
| Polyphase AF-1 | 9.000 | 9.000 |
| Barlox12 | 61.750 | 61.750 |
| Glycol DPM | 8.250 | 8.250 |
| Surfactant | 11.900 | 11.900 |
| Deodorizer | 1.000 | 1.000 |
| Defoamer | 0.100 | 0.100 |
| TOTAL WEIGHT | 100.000 | 100.000 |
| AMICAL | 1.000 |  |
| IPBC | 3.500 |  |
| Propiconazole | 3.500 |  |
| Amine Oxide | 37.050 |  |
| Total Actives | 45.050 |  |

Example 2

Antisapstain Control—Laboratory Test

1. Samples were Prepared as Follows:

Samples were taken from Red Pine branches approximately 10 mm in diameter after the bark was removed and cut into 2-4 mm thickness. Samples were treated (30 second dip) in the various preservative treatments and then allowed to air dry for one hour. Samples were then put into the test and were not sterilized.

2. Preparation of Cultures

Pure or group cultures were propagated at least four days in advance on a 7 cm filter paper soaked with 3 ml nutrient solution in a test tube. After growth covered the filter paper, 15 ml of sterile distilled water was added to the tube and macerated until the sample was homogenized.

3. Preparation of Test Chamber

The test chamber was a petri dish with a connecting duct to a water reservoir and a lid with an 0.2 mm micropore vapor port. The reservoir was taped to the petri dish with heat resistant tape, and then filled with distilled water. A piece of cellulose sponge was inserted into the reservoir duct. These dishes were sterilized in an autoclave for 45 minutes at 121° C. Next, an adequate number (about 50) of ashless 7 cm filter paper was placed in a container of nutrient solution, which was then sterilized in the autoclave for 45 minutes at 121° C. Three pieces of ashless 7 cm filter paper soaked in nutrient solution were added to the dish, making sure that the filter paper and sponge made contact and that the filter paper was centered in the dish.

4. Test Completion

Samples were added to the test chamber, out of contact with each other and arranged in a circular pattern within the chamber. The samples were not sitting on the filter paper, but overlapped the paper by a few millimeters. Culture inoculum, 1.0 ml deuteromycete fungi blend, was added to the center of the filter paper. The dishes were then incubated at 26°-32° C. and 70%-90% relative humidity.

5. Evaluation

At five and fifteen days, the samples were evaluated. Evaluations were made visually using a scale from −10 to 10. Minus ten (−10) indicates an inhibitory zone around the sample, and the sample is not infected. Ten (10) indicates a sample covered with mycellium.

Analysis of Results

Evaluations were converted from the scale (−10 to 10) to express percentage of wood surface area protected using the following equation: [(Visual Evaluation)−10]×(−10)=Percentage of wood Surface Area Protected. After conversions, one way analyses of variance (ANOVA) and Student's t-Test were used to test for treatment differences at a determined rate of probability. A percent protection level that is greater than 100% indicates that a zone of inhibition was provided around the sample. The maximum value is 200%.

| Fungi used for Testing | | | |
| --- | --- | --- | --- |
| Economic Class | Biological Class | Organism | ATC Number |
| Soft Rot | Deuteromycete | *Acremonium strictum* | A10141 |
| Soft Rot |  | *Chaetomium globosum* | 6021 |
| Soft Rot |  | *Graphium rubrum* | 6506 |

Fungi used for Testing

| Economic Class | Biological Class | Organism | ATC Number |
|---|---|---|---|
| Mold | | Trichoderma sp. | K2 |
| Mold | | Trichoderma viride | 13631 |
| Mold | | Aspergillus niger | A1004 |
| Mold | | Aspergillus sp. | K1 |
| Mold | | Paecilomyces varioti | 16023 |
| Mold | | Gliocladium sp. | K3 |
| Mold | | Cephaloascus fragrans | 24950 |
| Mold | | Alternaria alternata | 13963 |
| Mold | | Penicillium purpurogenum | 52427 |
| Mold | | Cladosporum cladosprioides | 16022 |
| Stain | Deuteromycete | Aureobasidium pullulans | 16622 |
| Stain | | Diplodia gossypina | 9055 |
| Stain | | Chlorociboria aeruginascens | 24028 |
| Stain | Ascomycete | Ceratocystis(Ophiostoma) picea | 387A |
| Stain | | Ceratocystis(Ophiostoma) fimbriata | 14503 |
| Stain | | Ceratocystis(Ophiostoma) clavigerum | 18086 |

TABLE 3

K-200 Laboratory Test Results

| Concentrations of Active Ingredients Diluted 50:1 v/v with water | | | | Percent Surface |
|---|---|---|---|---|
| Diiodomethyl-p-tolylsulfone | Pro-piconazole | 3-iodo-2-propynyl butyl carbamate | Amine Oxide | Protection-Deuteromycete Blend of Fungi |
| 1.0 | 3.5 | 3.5 | 37.05 | 108A |
| 8.0 | | | 37.05 | 91B |
| | 8.0 | | 37.05 | 90B |
| | | 8.0 | 37.05 | 92B |
| 1.0 | 3.5 | 3.5 | | 72C |
| | | | 45.05 | 60D |
| Untreated | | | | 0E |

Averages ending in the same letter are statistically equal at a 95% confidence level.

TABLE 4

| Concentrations of Active Ingredients Diluted 100:1 v/v with water | | | | Percent Surface |
|---|---|---|---|---|
| Diiodomethyl-p-tolylsulfone | Pro-piconazole | 3-iodo-2-propynyl butyl carbamate | Amine Oxide | Protection-Deuteromycete Blend of Fungi |
| 1.0 | 3.5 | 3.5 | 37.05 | 105A |
| 8.0 | | | 37.05 | 86B |
| | 8.0 | | 37.05 | 86B |
| | | 8.0 | 37.05 | 85B |
| 1.0 | 3.5 | 3.5 | | 65C |
| | | | 45.05 | 49D |
| Untreated | | | | 0E |

Averages ending in the same letter are statistically equal at a 95% confidence level.

TABLE 5

| Concentrations of Active Ingredients Diluted 150:1 v/v with water | | | | Percent Surface |
|---|---|---|---|---|
| Diiodomethyl-p-tolylsulfone | Pro-piconazole | 3-iodo-2-propynyl butyl carbamate | Amine Oxide | Protection-Deuteromycete Blend of Fungi |
| 1.0 | 3.5 | 3.5 | 37.05 | 100A |
| 8.0 | | | 37.05 | 79B |
| | 8.0 | | 37.05 | 66C |
| | | 8.0 | 37.05 | 82B |
| 1.0 | 3.5 | 3.5 | | 42D |
| | | | 45.05 | 45D |
| Untreated | | | | 0E |

Averages ending in the same letter are statistically equal at a 95% confidence level.

TABLE 6

| Concentrations of Active Ingredients Diluted 200:1 v/v with water | | | | Percent Surface |
|---|---|---|---|---|
| Diiodomethyl-p-tolylsulfone | Pro-piconazole | 3-iodo-2-propynyl butyl carbamate | Amine Oxide | Protection-Deuteromycete Blend of Fungi |
| 1.0 | 3.5 | 3.5 | 37.05 | 95A |
| 8.0 | | | 37.05 | 70B |
| | 8.0 | | 37.05 | 59C |
| | | 8.0 | 37.05 | 74B |
| 1.0 | 3.5 | 3.5 | | 39D |
| | | | 45.05 | 32D |
| Untreated | | | | 0E |

Averages ending in the same letter are statistically equal at a 95% confidence level.

TABLE 7

| Concentrations of Active Ingredients Diluted 300:1 v/v with water | | | | Percent Surface |
|---|---|---|---|---|
| Diiodomethyl-p-tolylsulfone | Pro-piconazole | 3-iodo-2-propynyl butyl carbamate | Amine Oxide | Protection-Deuteromycete Blend of Fungi |
| 1.0 | 3.5 | 3.5 | 37.05 | 79A |
| 8.0 | | | 37.05 | 49B |
| | 8.0 | | 37.05 | 45BC |
| | | 8.0 | 37.05 | 56B |
| 1.0 | 3.5 | 3.5 | | 332C |
| | | | 45.05 | 12DE |
| Untreated | | | | 0E |

Averages ending in the same letter are statistically equal at a 95% confidence level.

TABLE 8

Bioassay Results

| Concentrations of Active Ingredients Diluted 150:1 v/v with Water | | | | Percent Surface Protection- |
|---|---|---|---|---|
| Diiodomethyl-p-tolylsulfone | Propiconazole | 3-iodo-2-propynyl Butyl Carbamate | Amine Oxide | Deuteromycete Blend of Fungi |
| 8.0(0.053) | | | | 37E |
| 4.0(0.027) | | | | 34E |
| 2.0(0.013) | | | | 12F |
| | 8.0(0.053) | | | 79C |
| | 4.0(0.027) | | | 62D |
| | 2.0(0.013) | | | 12F |
| | | 8.0(0.053) | | 86B |
| | | 4.0(0.027) | | 69DC |
| | | 2.0(0.013) | | 31E |
| | | | 22.525(0.150) | 13F |
| | | | 37.05(0.247) | 48D |
| | | | 45.05(0.300) | 51D |
| | | | 67.575(0.451) | 59D |
| 8.0(0.053) | | | 37.05(0.247) | 75C |
| | 8.0(0.053) | | 37.05(0.247) | 82BC |
| | | 8.0(0.053) | 37.05(0.247) | 89B |
| 4.0(0.027) | | 4.0(0.027) | | 44D |
| 4.0(0.027) | 4.0(0.027) | | | 90B |
| 4.0(0.027) | 4.0(0.027) | | | 76C |
| 1.0(0.007) | 7.0(0.047) | | | 80BC |
| 1.0(0.007) | | 7.0(0.047) | | 84BC |
| 4.0(0.027) | | 4.0(0.027) | 37.05(0.247) | 92B |
| 4.0(0.027) | 4.0(0.027) | | 37.05(0.247) | 74C |
| 1.0(0.007) | 3.5(0.023) | 3.5(0.023) | | 46D |
| 1.0(0.007) | 7.0(0.047) | | 37.05(0.247) | 82BC |
| 1.0(0.007) | | 7.0(0.047) | 37.05(0.247) | 92B |
| 0.5(0.003) | 1.75(0.012) | 1.75(0.012) | 22.525(0.150) | 64CD |
| 1.0(0.007) | 3.5(0.023) | 3.5(0.023) | 37.05(0.247) | 102A |
| 1.0(0.007) | 3.5(0.023) | 3.5(0.023) | 45.05(0.300) | 104A |
| 1.5(0.01) | 5.25(0.035) | 5.25(0.035) | 67.575(0.451) | 112A |
| 0.25(002) | 0.875(0.0058) | 0.875(0.0058) | 37.05(0.451) | 73C |
| 0.5(0.003) | 1.75(0.012) | 1.75(0.012) | 37.05(0.247) | 89B |
| 1.0(0.007) | 3.5(0.023) | 3.5(0.023) | 37.05(0.247) | 100A |
| 1.5(0.01) | 5.25(0.035) | 5.25(0.035) | 37.05(0.247) | 105A |
| Untreated | | | | 0 |

Example 3

Field Test Data

The dimensions of the wood samples are typically 2 in. by 4 in. and 0.5 m in length. Hardboards such as Red Oak and Gum typically varied in width. Boards were cut and then randomly selected from the various wood species. 25 samples of each treatment were used for testing: An endeavor was made to select only sapwood to ensure heartwood had a minimal affect on later assessments.

Preservative retentions of solutions were taken at the beginning and at the end of testing. Solution pick-up is measured before and after wood samples are dipped into treating solution.

The following results in Table 9 show how the present invention provides unique protection against sapstain fungi in the field when compared to the industry standard NP-1 (7.6% IPBC, 64.8% DDAC).

Test samples were observed for fungal growth. The percentage of attack on the surface of the samples was recorded. A 0% (No attack)-100% (complete attack) rating scale was used.

TABLE 9

| | | Species | | | | | | | | | | | |
|---|---|---|---|---|---|---|---|---|---|---|---|---|---|
| | | Hemlock | | Douglas Fir | | Southern Yellow Pine | | Gum | | Red Oak | | Radiata Pine | |
| | | % v/v | * | % v/v | * | % v/v | * | % v/v | * | % v/v | * | % v/v | * |
| 7.6% IPBC, 64.8% DDAC | | | | | | | | | | | | | |
| 4weeks | | 1.0 | 9.3 | 1.0 | 13.2 | 1.0 | 22.0 | 0.67 | 45.2 | 0.67 | 2.0 | 1.0 | 1.1 |
| | | 0.67 | 12.3 | 0.67 | 16.0 | 0.67 | 35.2 | 0.5 | 30.0 | 0.5 | 12.0 | 0.67 | 5.0 |
| | | 0.5 | 36.2 | 0.5 | 36.0 | 0.5 | 38.0 | 0.4 | 29.2 | 0.4 | 18.0 | 0.5 | 8.0 |
| 12 weeks | | 1.0 | 17.0 | 1.0 | 16.8 | 1.0 | 39.75 | 0.67 | 52.0 | 0.67 | 5.0 | 1.0 | 5.0 |
| | | 0.67 | 24.8 | 0.67 | 28.32 | 0.67 | 43.25 | 0.5 | 45.5 | 0.5 | 15.0 | 0.67 | 8.0 |
| | | 0.5 | 40.97 | 0.5 | 52.16 | 0.5 | 45.50 | 0.4 | 37.25 | 0.4 | 25.5 | 0.5 | 12.0 |

TABLE 9-continued

| | | Hemlock | | Douglas Fir | | Southern Yellow Pine | | Gum | | Red Oak | | Radiata Pine | |
|---|---|---|---|---|---|---|---|---|---|---|---|---|---|
| | | % v/v | * | % v/v | * | % v/v | * | % v/v | * | % v/v | * | % v/v | * |
| 1.0% DIMPS, 3.5% IPBC, 3.5% Propiconazole, 37.05% Amine Oxide | | | | | | | | | | | | | |
| 4 weeks | | 1.0 | 5.0 | 1.0 | 15.2 | 1.0 | 8.0 | 0.67 | 2.0 | 0.67 | 0.0 | 1.0 | 1.0 |
| | | 0.67 | 8.2 | 0.67 | 16.2 | 0.67 | 12.0 | 0.5 | 1.9 | 0.5 | 8.0 | 0.67 | 2.0 |
| | | 0.5 | 9.2 | 0.5 | 24.2 | 0.5 | 18.0 | 0.4 | 4.0 | 0.4 | 10.0 | 0.5 | 3.0 |
| 12 weeks | | 1.0 | 11.84 | 1.0 | 23.28 | 1.0 | 14.75 | 0.67 | 3.75 | 0.67 | 0.5 | 1.0 | 2.0 |
| | | 0.67 | 15.56 | 0.67 | 23.92 | 0.67 | 38.0 | 0.5 | 4.00 | 0.5 | 20.0 | 0.67 | 3.2 |
| | | 0.5 | 15.52 | 0.5 | 27.76 | 0.5 | 38.25 | 0.4 | 8.50 | 0.4 | 17.0 | 0.5 | 5.0 |
| 2.0% DIMPS, 3.0% IPBC | | | | | | | | | | | | | |
| 4 weeks | | 1.0 | 22.0 | 1.0 | 25.2 | 1.0 | 32.0 | 0.67 | 12.0 | 0.67 | 31.2 | 1.0 | 15.0 |
| | | 0.67 | 45.2 | 0.67 | 45.2 | 0.67 | 55.0 | 0.5 | 26.3 | 0.5 | 44.1 | 0.67 | 16.0 |
| | | 0.5 | 42.1 | 0.5 | 49.3 | 0.5 | 62.0 | 0.4 | 42.0 | 0.4 | 49.0 | 0.5 | 22.0 |
| 12 weeks | | 1.0 | 38.0 | 1.0 | 36.2 | 1.0 | 62.0 | 0.67 | 33.5 | 0.67 | 47.4 | 1.0 | 22.0 |
| | | 0.67 | 50.0 | 0.67 | 57.8 | 0.67 | 65.0 | 0.5 | 31.8 | 0.5 | 52.0 | 0.67 | 18.0 |
| | | 0.5 | 45.0 | 0.5 | 54.6 | 0.5 | 72.0 | 0.4 | 45.3 | 0.4 | 55.1 | 0.5 | 39.0 |
| 4.0% IPBC | | | | | | | | | | | | | |
| 4 weeks | | 1.0 | 22.2 | 1.0 | 36.2 | 1.0 | 40.0 | 0.67 | 19.0 | 0.67 | 12.0 | 1.0 | 42.0 |
| | | 0.67 | 26.3 | 0.67 | 45.2 | 0.67 | 55.3 | 0.5 | 22.0 | 0.5 | 32.0 | 0.67 | 51.0 |
| | | 0.5 | 45.2 | 0.5 | 55.2 | 0.5 | 65.1 | 0.4 | 35.1 | 0.4 | 35.0 | 0.5 | 63.1 |
| 12 weeks | | | | | | | | | | | | | |
| 4.0% IPBC, 27.0% Amine Oxide | | | | | | | | | | | | | |
| 4 weeks | | 1.0 | 12.2 | 1.0 | 36.2 | 1.0 | 12.0 | 0.67 | 5.9 | 0.67 | 5.0 | 1.0 | 28.0 |
| | | 0.67 | 15.2 | 0.67 | 45.2 | 0.67 | 26.3 | 0.5 | 7.2 | 0.5 | 16.0 | 0.67 | 32.0 |
| | | 0.5 | 25.3 | 0.5 | 49.2 | 0.5 | 42.0 | 0.4 | 9.0 | 0.4 | 22.0 | 0.5 | 45.2 |
| 12 weeks | | 1.0 | 20.7 | 1.0 | 47.4 | 1.0 | 33.5 | 0.67 | 9.3 | 0.67 | 15.0 | 1.0 | 35.0 |
| | | 0.67 | 28.7 | 0.67 | 52.0 | 0.67 | 31.8 | 0.5 | 13.4 | 0.5 | 32.0 | 0.67 | 55.0 |
| | | 0.5 | 53.9 | 0.5 | 55.12 | 0.5 | 45.3 | 0.4 | 16.0 | 0.4 | 38.0 | 0.5 | 62.0 |
| 5.0% DIMPS | | | | | | | | | | | | | |
| 4 weeks | | 1.0 | 26.2 | 1.0 | 36.2 | 1.0 | 32.0 | 0.67 | 34.2 | 0.67 | 12.0 | 1.0 | 10.0 |
| | | 0.67 | 29.2 | 0.67 | 45.2 | 0.67 | 45.0 | 0.5 | 41.1 | 0.5 | 16.0 | 0.67 | 6.0 |
| | | 0.5 | 46.3 | 0.5 | 45.9 | 0.5 | 60.0 | 0.4 | 47.1 | 0.4 | 21.0 | 0.5 | 20.0 |
| 12 weeks | | 1.0 | 49.3 | 1.0 | 51.8 | 1.0 | 52.0 | 0.67 | 46.0 | 0.67 | 22.5 | 1.0 | 33.0 |
| | | 0.67 | 47.4 | 0.67 | 54.4 | 0.67 | 62.0 | 0.5 | 52.1 | 0.5 | 20.0 | 0.67 | 11.1 |
| | | 0.5 | 45.5 | 0.5 | 50.7 | 0.5 | 75.0 | 0.4 | 53.0 | 0.4 | 32.5 | 0.5 | 32.0 |

*Rating System = 0-100 Percent Attack
v/v = volume liquid / volume liquid basis

It will be appreciated that the present invention provides a wood treatment material having a synergistic combination of fungicides including an azole compound, a halopropynyl compound, an amine-oxide, and diiodomethyl-p-tolylsulfone, which is especially effective in providing resistance to decay, mold and mildew when wood is treated with this combination. While particular embodiments of this invention have been described above for purposes of illustration, it will be evident to those skilled in the art that numerous variations of the details of the present invention may be made without departing from the invention as defined in the appended claims.

We claim:

1. A fungicide treated wood protected against fungal decay, mold and mildew comprising wood treated with a composition in concentrate form consisting essentially of from about 0.1 to 10% by weight of an azole compound, about 0.1 to 10% by weight of a halopropynyl compound, about 0.1 to 10% by weight of diiodomethyl-p-tolylsulfone, and about 5 to 90% by weight of an amine oxide, based upon 100% by weight of the total wood treatment composition.

2. The wood of claim 1, wherein the azole compound is a 1,2,4-triazole.

3. The wood of claim 2, wherein the azole is selected from the group consisting of triadimefon, triazbutil, propiconazole, cyproconazole, difenoconazole, fluquinoconazole, tebuconazole, flusiazole, uniconazole, diniconazole, bitertanol, hexaconazole, azaconazole, flutriafol, epoxiconazole, tetraconazole, penconazole, and mixtures thereof.

4. The wood of claim 3, wherein the azole is propiconazole.

5. The wood of claim 3, wherein the azole is selected from the group consisting of azaconazole and hexaconazole.

6. The wood of claim 1, wherein the halopropynyl compound is represented by the formula:

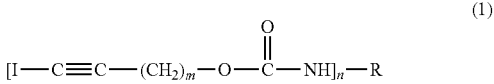

(1)

and R is selected from the group consisting of hydrogen, substituted and unsubstituted alkyl groups having from 1 to 20 carbon atoms, substituted and unsubstituted aryl, alkylaryl, and aralkyl groups having from 6 to 20 carbon atoms and from substituted and unsubstituted cycloalkyl and cycloalkenyl groups of 3 to 10 carbon atoms, and m and n are independently integers from 1 to 3.

7. The wood of claim 6, wherein the halopropynyl compound is selected from the group consisting of 3-iodo-2-propynyl propyl carbamate, 3-iodo-2-propynyl butyl carbamate, 3-iodo-2-propynyl hexyl carbamate, 3-iodo-2-propynyl cyclohexyl carbamate, 3-iodo-2-propynyl phenyl carbamate, and mixtures thereof.

8. The wood of claim 7, wherein the halopropynyl compound is 3-iodo-2-propynyl butyl carbamate.

9. The wood of claim 1, wherein the amine oxide compound is represented by the formula:

(3)

where R1, R2 and R3 are independent and can be linear, branched, cyclic, aromatic or any combination thereof of saturated or unsaturated C1 to C20 group and any C2-C20 carbon atom can be replaced with a heteroatom selected from the group consisting of O, S and N.

10. The wood of claim 9, wherein the amine oxide compound is selected from the group consisting of decyl dimethyl amine oxide, lauryl dimethyl amine oxide, isoalkyl dimethyl amine oxide, myristyl dimethyl amine oxide, cetyl dimethyl amine oxide, stearyl dimethyl amine oxide, octyl dimethyl amine oxide, N-alkyl(C12-C16)-N,N-dimethylamine oxide and mixtures thereof.

11. The wood of claim 10, wherein the amine oxide compound is N-alkyl(C12-C16)-N,N-dimethylamine oxide.

12. The wood of claim 1, wherein the composition further consists essentially of a solvent.

13. The wood of claim 12, wherein the solvent is selected from the group consisting of alcohols, glycols, esters, ethers, polyethers, and mixtures thereof.

14. The wood of claim 1, wherein the composition further consists essentially of water.

15. The wood of claim 1, wherein the composition further consists essentially of an additive.

16. The wood of claim 15, wherein the additive is selected from the group consisting of a corrosion inhibitor, iron stain inhibitor, wetting agent, colorant, adhesive, emulsifier, filler, carrier, viscosity regulator, pH regulator, binder, tackifier, and mixtures thereof.

17. The wood of claim 1, wherein the wood is engineered wood.

18. A fungicide treated wood protected against fungal decay, mold and mildew comprising wood treated with a composition in concentrate form consisting essentially of from about 0.1 to 10% by weight of propiconazole, about 0.1 to 10% by weight of a 3-Iodo-2-Propynyl butyl carbamate, about 0.1 to 10% by weight of diiodomethyl-p-tolylsulfone, and about 5 to 90% by weight of an amine oxide, based upon 100% by weight of the total wood treatment composition.

* * * * *

UNITED STATES PATENT AND TRADEMARK OFFICE
CERTIFICATE OF CORRECTION

PATENT NO. : 8,664,250 B1
APPLICATION NO. : 11/130526
DATED : March 4, 2014
INVENTOR(S) : Alan S. Ross et al.

Page 1 of 4

It is certified that error appears in the above-identified patent and that said Letters Patent is hereby corrected as shown below:

In the Specification
Column 3, line 61, "furnish" should read --finish--.
Column 5, line 60, "in art" should read --in the art--.
Column 6, line 61, "62.00°g" should read --62.00g--.
Column 7, line 4, "carbam-" should read --carba- --.
Column 7, line 5, "ate" should read --mate--.
Column 7, line 6, "solution is clear" should read --solution was clear--.
Column 8, line 64, "Soft Rot     Deuteromycete     *Acremonium strictum*     A10141"
should read
            --Deuteromycete
Soft Rot                              *Acremonium strictum*     A10141--.

Column 9, line 19,
"Stain        Deuteromycete     *Aureobasidium pullulans*     16622"
should read
            --Deuteromycete
Stain                                 *Aureobasidium pullulans*     16622--.

Column 9, lines 22 and 23,
"Stain        Ascomycete        *Ceratocystis (Ophiostoma)*     387A
                                *picea*"
should read
            --Ascomycete
Stain                                 *Ceratocystis (Ophiostoma)*     387A
                                      *picea*--.

Signed and Sealed this
Twenty-fourth Day of June, 2014

Michelle K. Lee
*Deputy Director of the United States Patent and Trademark Office*

Column 9, TABLE 3, lines 36 through 41,

"
TABLE 3

K-200 Laboratory Test Results

| Concentrations of Active Ingredients Diluted 50:1 v/v with water | | | | Percent Surface Protection- Deuteromycete Blend of Fungi |
|---|---|---|---|---|
| Diiodomethyl- p-tolylsulfone | Pro- piconazole | 3-iodo-2- propynyl butyl carbamate | Amine Oxide | |

"

should read

*TABLE 3*

| Concentrations of Active Ingredients Diluted 50:1 v/v with water | | | | Percent Surface Protection- Deuteromycete Blend of Fungi |
|---|---|---|---|---|
| Diiodomethyl- p-tolysulfone | Propiconazole | 3-iodo-2- propynyl butyl carbamate | Amine Oxide | |

--.

Column 9, TABLE 4, lines 54 through 58,

TABLE 4

"

| Concentrations of Active Ingredients Diluted 100:1 v/v with water | | | | Percent Surface Protection- Deuteromycete Blend of Fungi |
|---|---|---|---|---|
| Diiodomethyl- p-tolylsulfone | Pro- piconazole | 3-iodo-2- propynyl butyl carbamate | Amine Oxide | |

"

should read

TABLE 4

| Concentrations of Active Ingredients Diluted 100:1 v/v with water | | | | Percent Surface Protection- Deuteromycete Blend of Fungi |
|---|---|---|---|---|
| Diiodomethyl- p-tolysulfone | Propiconazole | 3-iodo-2- propynyl butyl carbamate | Amine Oxide | |

--.

Column 10, TABLE 5, lines 5 through 9,

TABLE 5

"

| Concentrations of Active Ingredients Diluted 150:1 v/v with water | | | | Percent Surface Protection- Deuteromycete Blend of Fungi |
|---|---|---|---|---|
| Diiodomethyl- p-tolylsulfone | Pro- piconazole | 3-iodo-2- propynyl butyl carbamate | Amine Oxide | |

"

should read

TABLE 5

| | Concentrations of Active Ingredients Diluted 150:1 v/v with water | | | Percent Surface Protection- Deuteromycete Blend of Fungi |
|---|---|---|---|---|
| Diiodomethyl- p-tolysulfone | Propiconazole | 3-iodo-2- propynyl butyl carbamate | Amine Oxide | |
| -- | | | | --. |

Column 10, TABLE 6, lines 27 through 31,

TABLE 6

| | Concentrations of Active Ingredients Diluted 200:1 v/v with water | | | Percent Surface Protection- Deuteromycete Blend of Fungi |
|---|---|---|---|---|
| Diiodomethyl- p-tolylsulfone | Pro- piconazole | 3-iodo-2- propynyl butyl carbamate | Amine Oxide | |

"                                                              "

should read

TABLE 6

| | Concentrations of Active Ingredients Diluted 200:1 v/v with water | | | Percent Surface Protection- Deuteromycete Blend of Fungi |
|---|---|---|---|---|
| Diiodomethyl- p-tolysulfone | Propiconazole | 3-iodo-2- propynyl butyl carbamate | Amine Oxide | |
| -- | | | | --. |

Column 10, TABLE 7, lines 51-55,

TABLE 7

| | Concentrations of Active Ingredients Diluted 300:1 v/v with water | | | Percent Surface Protection- Deuteromycete Blend of Fungi |
|---|---|---|---|---|
| Diiodomethyl- p-tolylsulfone | Pro- piconazole | 3-iodo-2- propynyl butyl carbamate | Amine Oxide | |

"                                                              "

should read

TABLE 7

| | Concentrations of Active Ingredients Diluted 300:1 v/v with water | | | Percent Surface Protection- Deuteromycete Blend of Fungi |
|---|---|---|---|---|
| Diiodomethyl- p-tolysulfone | Propiconazole | 3-iodo-2- propynyl butyl carbamate | Amine Oxide | |
| -- | | | | --. |

Column 11, TABLE 8, lines 3-7,

| TABLE 8 | | | | |
|---|---|---|---|---|
| Bioassay Results | | | | |
| Concentrations of Active Ingredients Diluted 150:1 v/v with Water | | | | Percent Surface Protection- |
| Diiodomethyl-p-tolylsulfone | Propiconazole | 3-iodo-2-propynyl Butyl Carbamate | Amine Oxide | Deuteromycete Blend of Fungi | should read

| TABLE 8 | | | | |
|---|---|---|---|---|
| Bioassay Results | | | | |
| Concentrations of Active Ingredients Diluted 150:1 v/v with water | | | | Percent Surface Protection- Deuteromycete Blend of Fungi |
| Diiodomethyl-p-tolysulfone | Propiconazole | 3-iodo-2-propynyl Butyl Carbamate | Amine Oxide | |

Column 11, TABLE 8, line 26,

"4.0(0.027)         4.0(0.027)    37.05(0.247)  92B"

should read

--4.0(0.027)        4.0(0.027)    37.05(0.247)  92B--.

Column 11, line 48, "testing:" should read --testing.--.

Column 11, line 50, "minimal affect" should read --minimal effect--.